United States Patent
Corr et al.

(10) Patent No.: US 6,756,023 B1
(45) Date of Patent: Jun. 29, 2004

(54) REACTOR COMPRISING A CONTACT TUBE BUNDLE

(75) Inventors: Franz Corr, Ludwigshafen (DE); Gerhard Olbert, Dossenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/744,447

(22) PCT Filed: Aug. 6, 1999

(86) PCT No.: PCT/EP99/05701
§ 371 (c)(1),
(2), (4) Date: Jan. 24, 2001

(87) PCT Pub. No.: WO00/09253
PCT Pub. Date: Feb. 4, 2000

(30) Foreign Application Priority Data

Aug. 13, 1998 (DE) .......................... 198 36 792

(51) Int. Cl.[7] .................................. B01J 8/06
(52) U.S. Cl. .................. 422/198; 422/201; 422/202; 422/205
(58) Field of Search .................. 422/188, 196, 422/197, 198, 201, 202, 203, 205, 211, 234

(56) References Cited

U.S. PATENT DOCUMENTS

| 2,098,148 A | | 11/1937 | Jarl ............................ 23/288 |
| 3,566,961 A | | 3/1971 | Lorenz ....................... 165/159 |
| 3,760,870 A | | 9/1973 | Guetlhuber .................. 165/35 |
| 3,807,963 A | * | 4/1974 | Smith ......................... 422/197 |
| 3,871,445 A | | 3/1975 | Wanka et al. ............... 165/107 |
| 4,337,224 A | * | 6/1982 | Mahler et al. .............. 422/197 |
| 4,657,741 A | | 4/1987 | Vogl ............................ 422/202 |
| 5,228,315 A | | 7/1993 | Nagasaka et al. .............. 62/509 |
| 5,739,391 A | | 4/1998 | Ruppel et al. ............... 562/532 |
| 6,582,667 B1 | * | 6/2003 | Ogata et al. ................. 422/201 |
| 6,645,443 B1 | * | 11/2003 | Vogel et al. ................. 422/200 |

FOREIGN PATENT DOCUMENTS

| DE | 16 01 162 | 10/1970 |
| DE | 2 201 528 | 11/1972 |
| DE | 34 09 159 | 9/1985 |
| DE | 44 31 949 | 3/1995 |
| GB | 310157 | 4/1929 |
| GB | 553107 | 5/1943 |

* cited by examiner

*Primary Examiner*—Kiley Stoner
*Assistant Examiner*—Len Tran
(74) *Attorney, Agent, or Firm*—Keil & Weinkauf

(57) ABSTRACT

The invention proposes a reactor (1) having a contact tube bundle (2) through whose space surrounding the contact tubes a heat-exchange medium circuit is passed, with ring lines (3, 4) at both ends of the reactor with jacket apertures (5, 6) for the supply and discharge of a heat-exchange medium by means of a pump via an external heat exchanger, where the heat-exchange medium is fed to the lower ring line (4) and is discharged to the heat exchanger via the upper ring line (3), and with baffle plates (7) which leave a passage cross section alternately in the reactor center and at the reactor edge. The upper (3) and lower (4) ring lines are each divided into an inner (11, 13) and an outer (12, 14) ring line by a cylindrical partition wall (8, 9), and the heat-exchange medium is fed to the outer lower ring line (14), via a region outside the reactor to the inner upper ring line (11), via the jacket apertures (5) of the latter to the region surrounding the contact tubes (2), via the jacket apertures (6) to the inner lower ring line (13) and subsequently via a region outside the reactor to the outer upper ring line (12).

8 Claims, 8 Drawing Sheets

REACTOR COMPRISING A CONTACT TUBE BUNDLE

Figure 1:
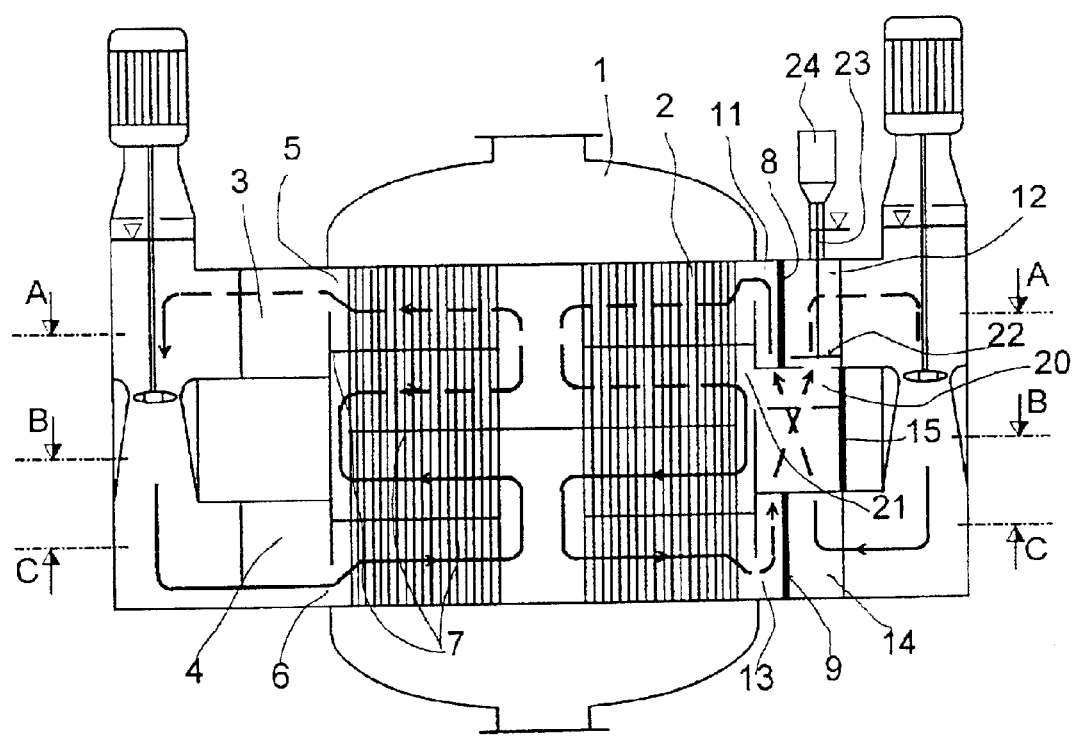

The invention relates to a reactor having a contact tube bundle through whose space surrounding the contact tubes a heat-exchange medium circuit is passed, and to the use of the reactor for carrying out oxidation reactions.

The conventional design of reactors of the generic type consists of a generally cylindrical tank in which a bundle, i.e. a multiplicity, of contact tubes is accommodated, usually in a vertical arrangement. These contact tubes, which may contain supported catalysts, are attached with their ends in tube bases in a sealing. manner and lead into a hood connected to the tank at the upper end and a hood connected to the tank at the lower end. The reaction mixture flowing through the contact tubes is fed in and led out via these hoods. A heat-exchange medium circuit passes through the space surrounding the contact tubes in order to equalize the heat balance, in particular in the case of highly exothermic reactions.

For economic reasons, reactors having the highest possible number of contact tubes are employed, the number of contact tubes accommodated frequently being in the range from 15000 to 30000 (cf. DE-A-44 31 949).

Regarding the heat-exchange medium circuit, it is known to implement a substantially homogeneous temperature distribution of the heat-exchange medium in each horizontal section through the reactor in order that wherever possible all the contact tubes participate equally in the reaction events (for example DE-B-16 01 162). Smoothing of the temperature distribution is effected by heat supply or dissipation via outer ring lines installed at the reactor ends and having a multiplicity of jacket apertures, as described, for example, in DE-B-34 09 159.

A further improvement in heat transfer is achieved by installation of baffle plates which leave a passage cross section alternately in the reactor center and at the reactor edge. Such an arrangement is particularly suitable for tube bundles in an annular arrangement with a free central space and is disclosed, for example, in GB-B-31 01 75.

In large reactors having a number of contact tubes in the abovementioned region of from about 15000 to 30000 and which are additionally equipped with baffle plates, the pressure drop of the heat-exchange medium is in comparative terms very large. For this reason, the eutectic salt melt comprising potassium nitrate and sodium nitrite which is frequently used to dissipate the heat liberated during oxidation reactions and has a viscosity similar to that of water at a use temperature of from to about 350 to 400° C. must be pumped into a reactor of the above size at a feed height of about 4 to 5 m in order to overcome the pressure drop.

In large reactors of this type, the pump system is advantageously located between the upper and lower ring line, with the heat-exchange medium being fed into the lower region of the reactor, for example via a ring line.

If, in large reactors of this type, the salt melt were to be pumped directly into the upper part of the reactor or the upper ring line, the requisite feed height of 4 to 5 m would require a technically unfavorable and fault-susceptible pump system, inter alia due to complex pump-shaft seals, longer pump shafts, and greater heat introduction through the pump shaft into the lower motor bearing. Furthermore, the abovementioned feed height would require a high-level salt-melt compensation vessel, which is undesired for safety reasons.

Supply of heat-exchange medium to the upper end of the reactor, i.e. in concurrent with the reaction mixture, likewise fed into the contact tubes at the upper end of the reactor, is, as is known, advantageous for reaction implementation (cf. DE-A-44 31 449).

The cocurrent implementation has advantages over the counter-current procedure, such as higher throughputs, lower catalyst hot-spot temperatures, a welcome increase in the heat-exchange medium temperature toward the end reaction in the contact tubes, good temperature uniformity of the heat-exchange medium over the reactor cross section, i.e. good horizontal temperature layering, clear operating states above the height of the contact tube space owing to the lack of back-coupling through the heat-exchange medium.

However, cocurrent transport of reaction mixture and heat-exchange medium, as described in DE-A44 31 449 or shown in DE-A-22 01 528, FIG. 1, comes up against the abovementioned problems regarding the pump system if the heat-exchange medium is fed to the upper region of the reactor, for example directly via an upper ring line, and discharged from the lower region of the reactor, for example directly via a ring line.

It is an object of the present invention to provide a reactor which does not have these disadvantages regarding the pump system. The pump system should not be modified compared with the design with feed of the heat-exchange medium into the lower ring line in the lower region of the reactor and discharged from the upper ring line which has proven successful for large reactors having a multiplicity of contact tubes, for example up to 40000, in particular from 15000 to 30000 contact tubes; nevertheless, the heat-exchange medium should flow around the contact tubes in cocurrent with the reaction mixture fed through the contact tubes.

We have found that this object is achieved by a reactor having a contact tube bundle through whose space surrounding the contact tubes a heat-exchange medium circuit is passed, with ring lines at both ends of the reactor with jacket apertures for the supply and discharge of a heat-exchange medium by means of one or more pumps, if desired with the heat-exchange medium or a substream of the heat-exchange medium being passed through one or more external heat exchangers, in which case the heat-exchange medium is fed to the lower ring line and fed back to the pump(s) via the upper ring line, and with baffle plates which leave a passage cross section alternately in the reactor center and the reactor edge, wherein the upper and lower ring lines are each divided into an inner and outer ring line by means of a cylindrical partition wall, and the heat-exchange medium is fed through the outer lower ring line, via a region outside the reactor to the inner upper ring line, via the latter's jacket apertures to the space surrounding the contact tubes, via jacket apertures into the inner lower ring line and subsequently via a region outside the reactor is discharged via the outer upper ring line.

It has been found that the space between the upper and lower ring lines can be utilized to divert the heat-exchange medium, allowing the advantage of cocurrent transport of heat-exchange medium and reaction mixture to be combined with the proven pump arrangement with feed of the heat-exchange medium to the lower ring line.

To this end, the invention provides that a cylindrical partition wall is arranged in the upper ring line and in the lower ring line, separating each of these lines into an inner and outer ring line. The heat-exchange medium is then fed to the outer lower ring line, which is connected to the inner upper ring line via the region between the upper and lower ring lines, from here is fed in a known manner via jacket apertures into the space surrounding the contact tubes, with a meander-like flow being formed in a known manner via baffle plates. The heat-exchange medium leaves the space surrounding the contact tubes, in the lower part of the reactor, in a known manner via jacket apertures and enters the lower inner ring line. This is in turn connected to the upper outer ring line via the region between the upper and lower ring lines.

The region between the upper and lower ring lines is advantageously closed by a cylinder envelope, forming a hollow cylinder, which is divided, by radial partition walls perpendicular to the reactor base, into chambers whose dividing walls to the ring lines leave alternately inner and outer circular ring sections, where, in plan view, an open circular ring section is always arranged above a closed circular ring section, and vice versa. The chambers thus always experience flow, from bottom to top, alternately by heat-exchange medium coming from the pump(s) and heat-exchange medium coming from the reactor space.

The number of chambers is in principle unlimited, but expediently a number of from 12 to 96, preferably from 24 to 48, can be provided, so that from 12 to 24 chambers (corresponding to from 3 to 6 chambers per quarter) are alternately available for the transport (redirection) of the heat-exchange medium to the inlet in the upper region of the reactor space surrounding the contact tubes and to the outlet from the lower region of same.

The cylindrical partition walls which separate each of the upper and lower ring lines into an inner and outer ring line may in principle have any diameter between the external and internal diameters of the ring lines. However, the diameter of the cylindrical partition walls is preferably less than or equal to the arithmetic mean of the outer and inner diameters of the ring lines.

In a preferred embodiment, a bypass chamber with jacket aperture to the reactor space and a regulating plate is arranged in the region of the outer upper ring line in each case in at least some of the chambers through which heat-exchange medium flows and is discharged to the pump(s), the position of the regulating plate being adjustable in the direction of the longitudinal axis of the reactor via an actuating drive and a drive spindle. In this configuration, an adjustable sub-stream of the heat-exchange medium coming from the reactor space can be taken off as early as the central height of the reactor, meaning that only the remaining volume of the heat-exchange medium flows through the lower part of the reactor space surrounding the contact tubes only experiences. This embodiment is optimized with respect to decreasing heat evolution in the lower part of the contact tubes. In addition, a reduction in the pressure drop is achieved, which permits reduced pump output and thus increased economic efficiency.

The reactor is not restricted with respect to the type of heat-exchange medium, which can be used equally to dissipate heat, i.e. for the performance of exothermic reactions, and for the supply of heat to the reaction mixture flowing through the contact tubes, i.e. for the performance of endothermic reactions.

The reactor is particularly suitable for the performance of oxidation reactions, in particular for the preparation of phthalic anhydride, maleic anhydride, glyoxal, (meth) acrolein and (meth)acrylic acid.

Figure 2:
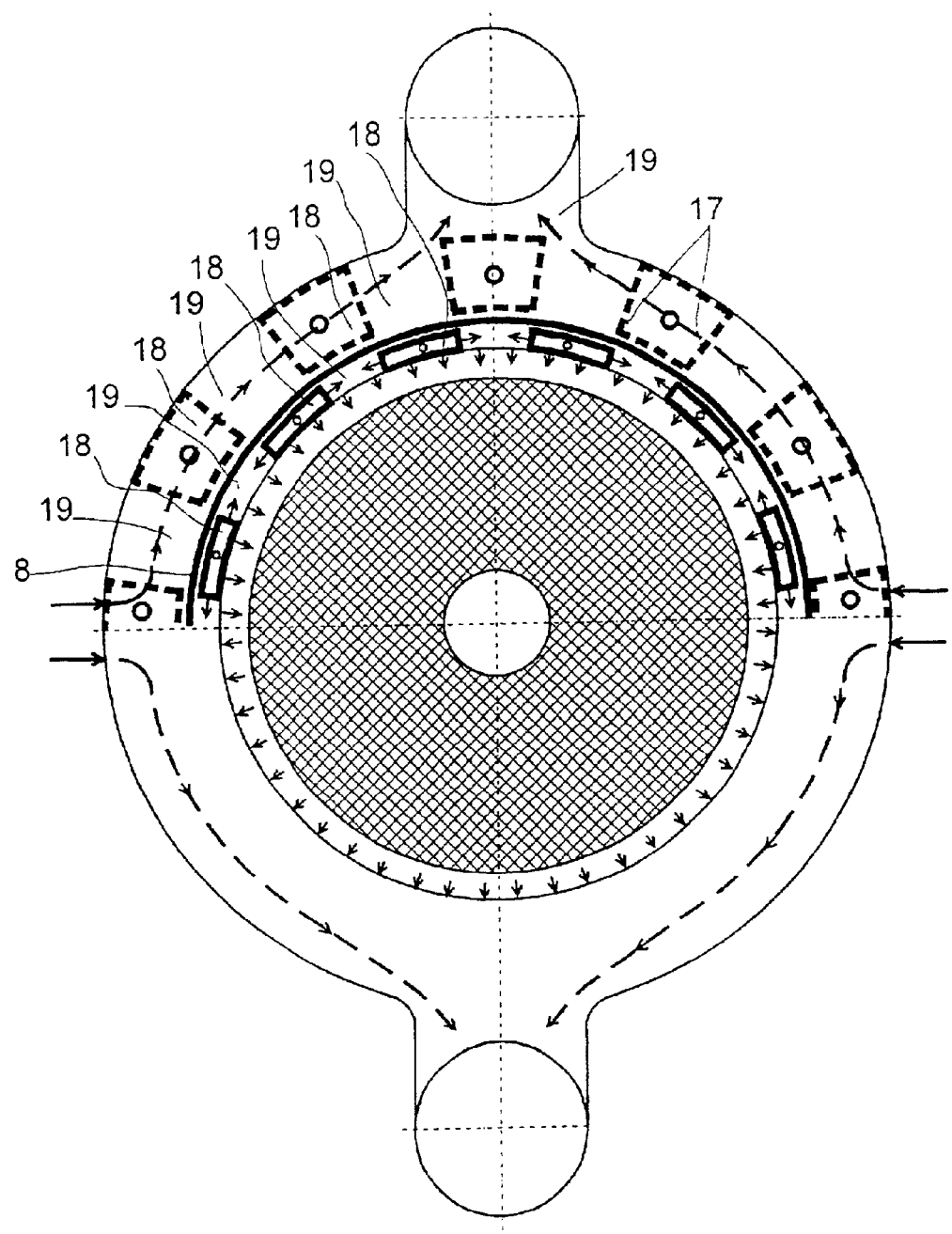
Figure 3:
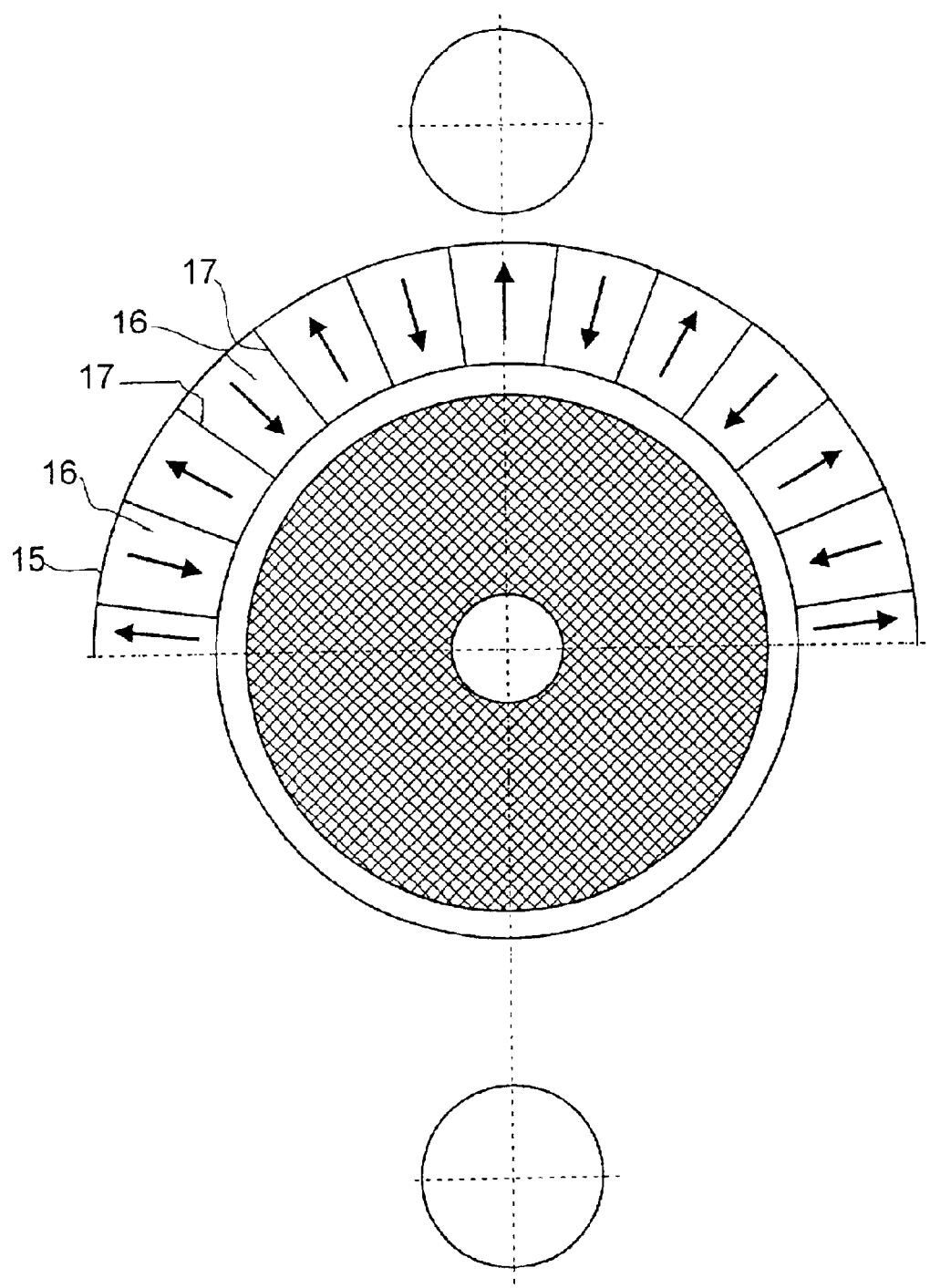
Figure 4:
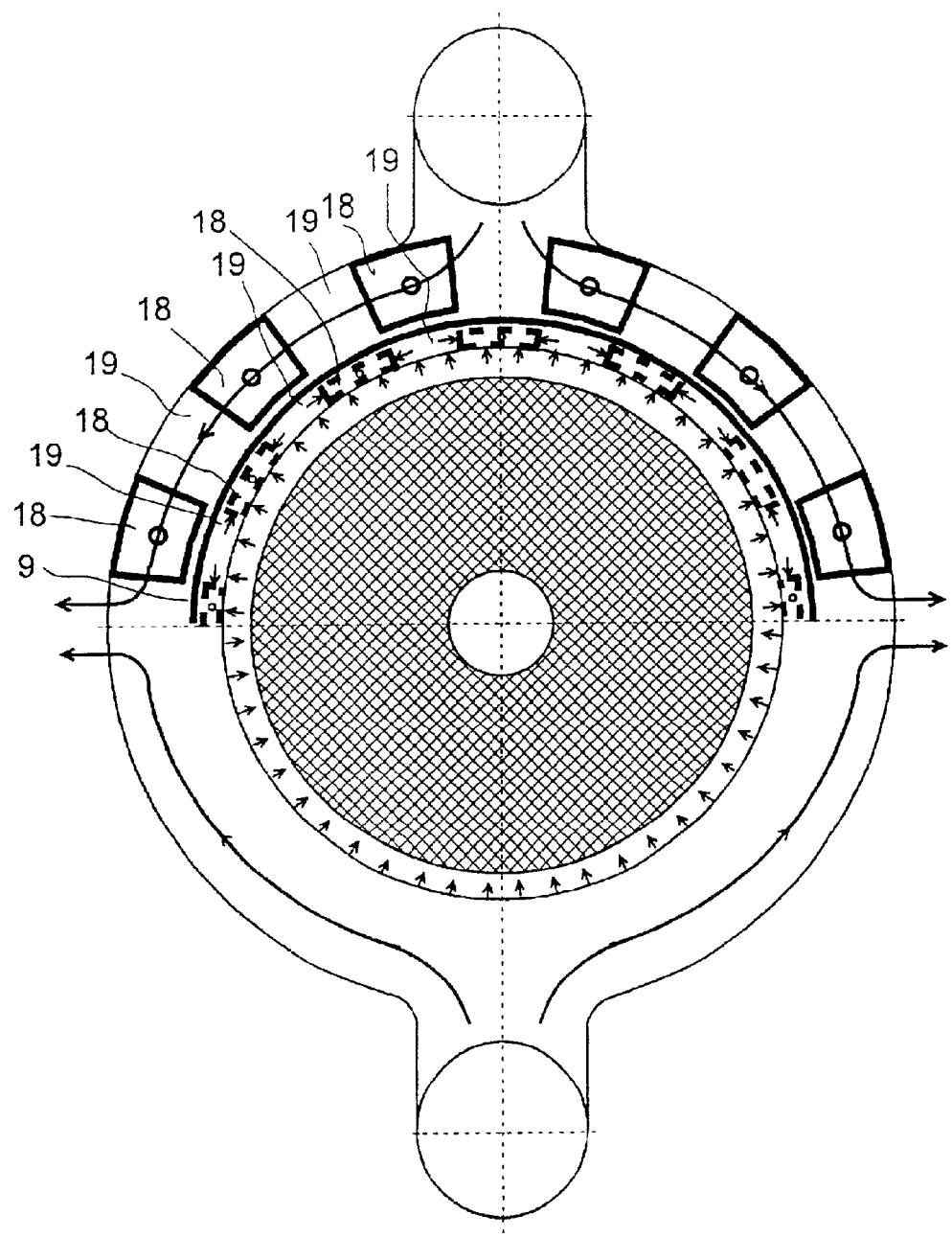
Figure 5:
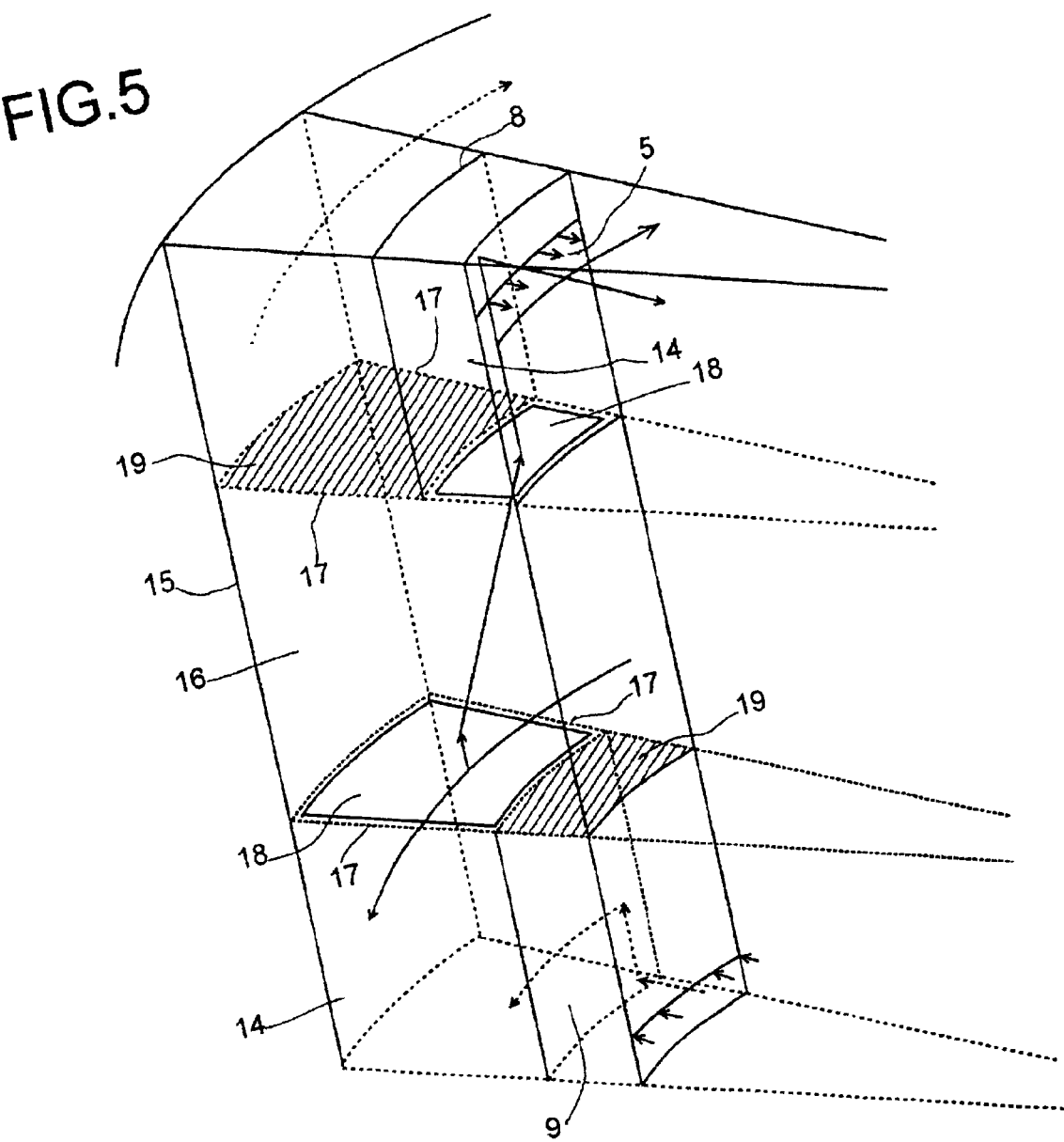
Figure 6:
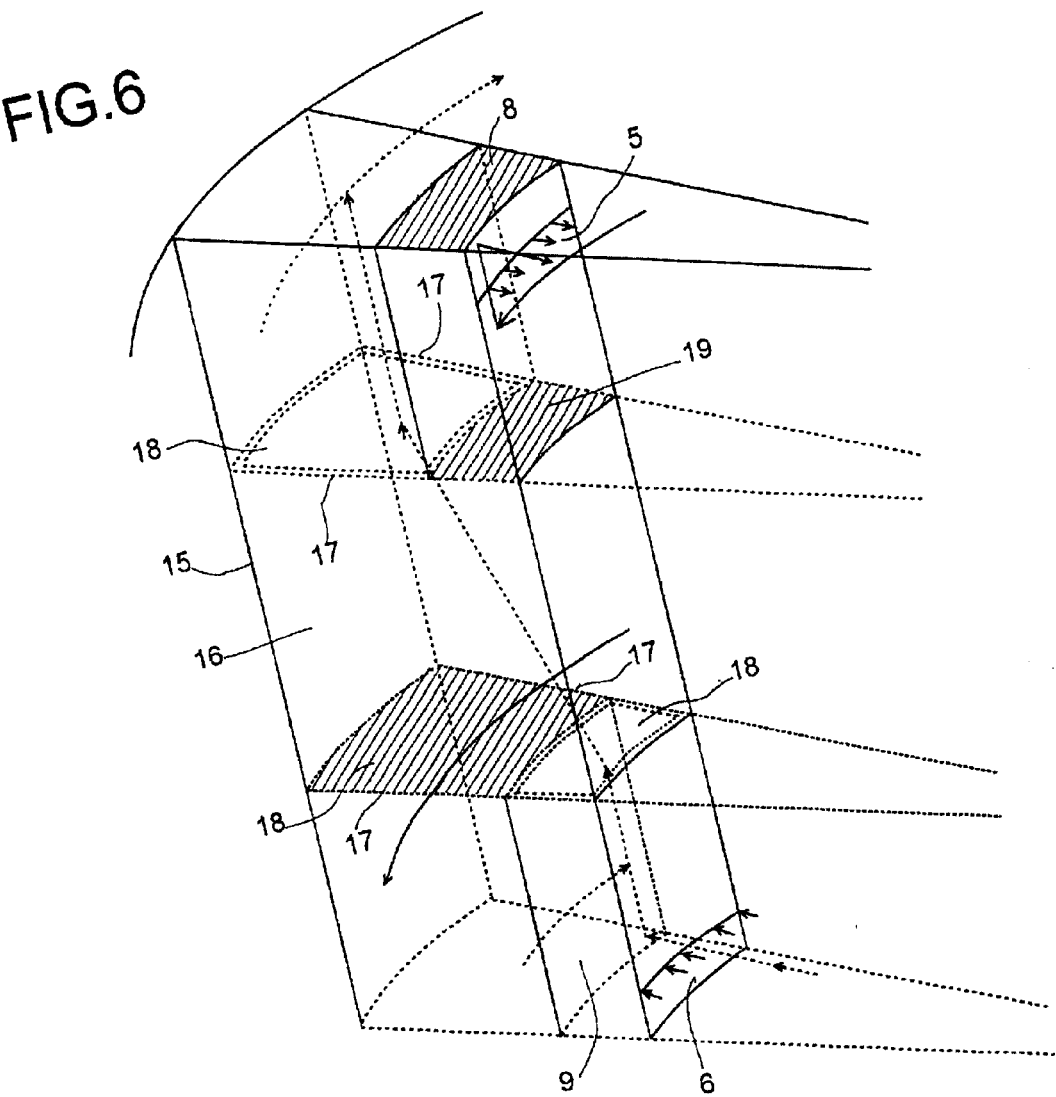
Figure 7:
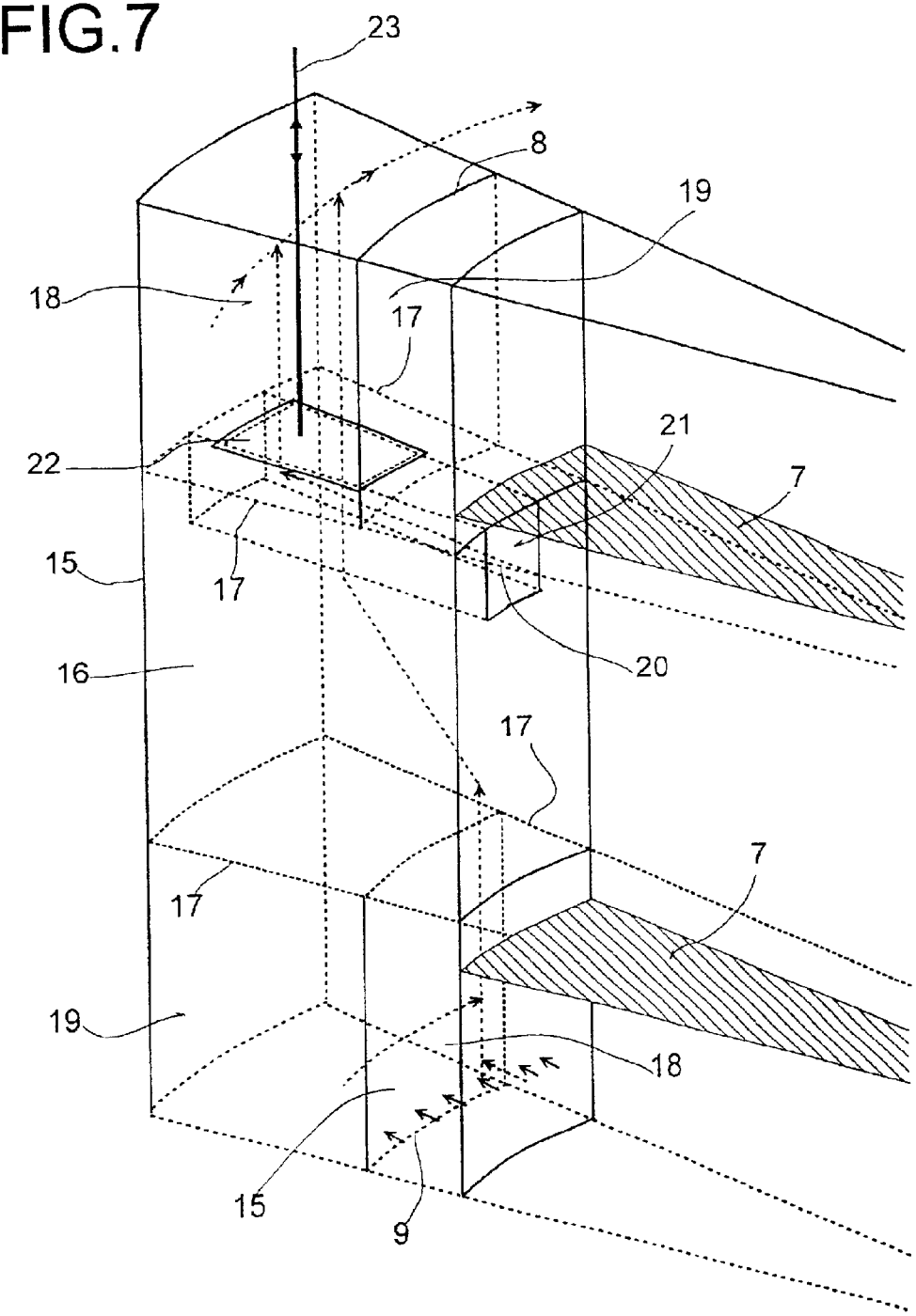
Figure 8:
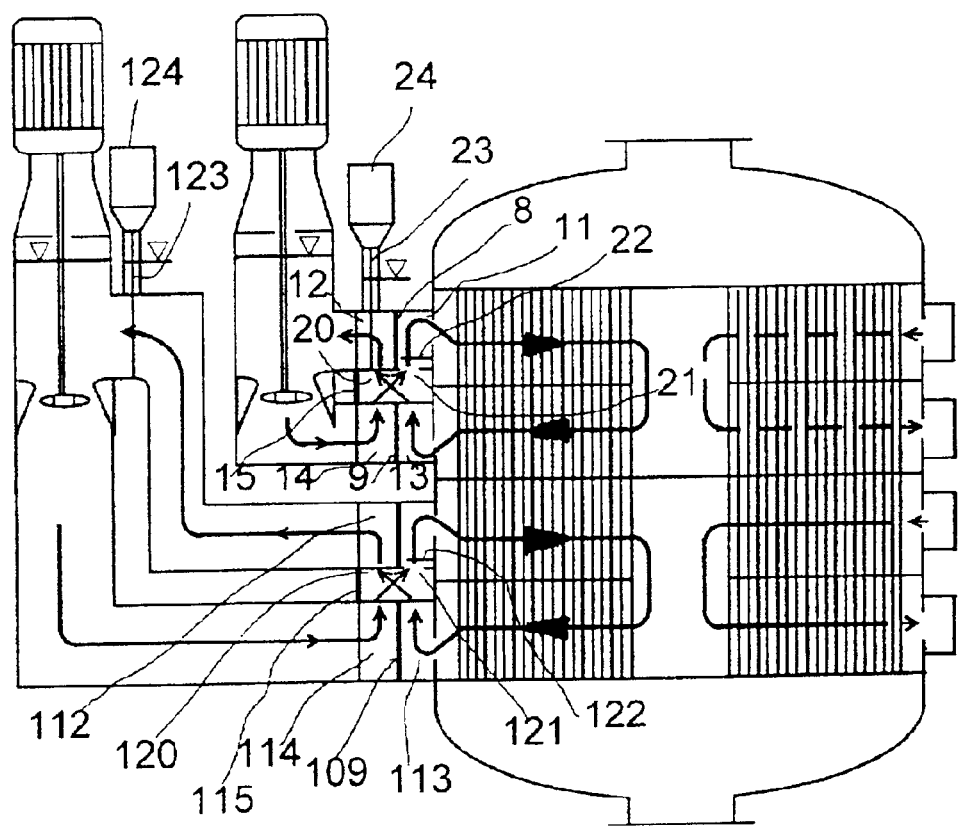

The invention is illustrated in greater detail below with reference to working examples and a drawing, in which:

FIG. 1, right-hand side: shows a longitudinal section through a reactor with heat-exchange medium circuit in accordance with the invention, FIG. 1, left-hand side: shows a longitudinal section through a reactor with heat-exchange medium circuit in accordance with the prior art, FIG. 2, right-hand side: shows a cross section through a reactor according to the invention in the region of the dividing area between the upper ring line and the central hollow cylinder (Section A—A), FIG. 2, left-hand side: shows a cross section in the plane A—A through a reactor in accordance with the prior art, FIG. 3, right-hand side: shows a cross section through a reactor according to the invention in the region of the central hollow cylinder (Section B—B), FIG. 3, left-hand side: shows a cross section in the plane B—B through a reactor in accordance with the prior art, FIG. 4, right-hand side: shows a cross section through a reactor according to the invention in the region of the separating area between the central hollow cylinder and the lower ring line (Section C—C), FIG. 4, left-hand side: shows a cross section in the plane C—C through a reactor in accordance with the prior art, FIG. 5: shows a detail of a reactor according to the invention in order to illustrate the feed of heat-exchange medium to the space surrounding the contact tubes, FIG. 6: shows a detail of a reactor according to the invention in order to illustrate the discharge of heat-exchange medium from the space surrounding the contact tubes to the pump(s), FIG. 7: shows a detail of a preferred embodiment of a reactor according to the invention, and FIG. 8: shows a cross section through a reactor according to the invention having two heat-exchange medium circuits.

FIG. 1 shows a cylindrical reactor 1 having a vertical contact tube bundle 2 which leaves an internal space in the center of the cylinder, with a lower ring line 4, to which heat-exchange medium is fed, and an upper ring line 3, through which heat-exchange medium is discharged, the feed and discharge of the heat-exchange medium taking place via jacket apertures 5 and 6, and with baffle plates 7, which produce a meander-shaped heat-exchange medium circuit.

To this extent, the design of the reactor in accordance with the prior art (left-hand side of FIG. 1) is identical with the design of the reactor in accordance with the invention (right-hand side of FIG. 1).

As can be seen on the right-hand side of FIG. 1, the reactor according to the invention has the following modifications compared with the prior art:

The upper ring line 3 is divided into an inner upper ring line 11 and an outer upper ring line 12 by a cylindrical partition wall 8; analogously, the lower ring line 4 is divided into an inner lower ring line 13 and an outer lower ring line 14 by the cylindrical partition wall 9.

The region between the ring lines 3 and 4 is preferably closed by a cylinder envelope 15 to form a hollow cylinder. This region is where the diversion of the heat-exchange medium from the outer lower ring line 14 to the inner upper ring line 11 or from the inner lower ring line 13 to the outer upper ring line 12 takes place. This diversion of heat-exchange medium in the region of the central hollow cylinder preferably takes place through the formation of chambers 16 by means of radial partition walls 17, which are perpendicular to the reactor base (FIG. 3).

The transport of the heat-exchange medium to the upper or lower ring line in the region of the dividing areas of the central hollow cylinder can be seen from the cross sections shown in FIG. 2, right, and FIG. 4, right: the cylindrical partition walls 8 and 9 and the radial partition walls 17 form inner and outer circular ring sections. As shown in FIG. 2, right, and FIG. 4, right, these are formed, according to the invention, alternately as open circular ring sections 18 and closed circular ring sections 19. In this connection, alternately means that on each inner or outer ring line an open circular ring section is followed by a closed circular ring section, and that in addition, in plan view, an open circular ring section 18 in the cross-sectional view A—A always corresponds to a closed circular ring section 19 in the cross-sectional view C—C, and vice versa. This design means that the chambers always experience passage, from bottom to top, alternately by heat-exchange medium coming from the pump(s) and heat-exchange medium coming from the reactor space, as shown in FIG. 3.

In order to illustrate the heat-exchange medium transport, sections of a reactor according to the invention are shown in FIGS. 5 and 6:

FIG. 5 shows a chamber 16 through which heat-exchange medium from the pump(s) flows via the lower outer ring line 14 through the open circular ring section 18 into the chamber 16 from bottom to top, the heat-exchange medium leaves in the upper region via a further open circular ring section 18, flows into the upper inner ring line 11 and is fed to the reactor space surrounding the contact tubes via the jacket aperture 5.

The chamber 16 shown in FIG. 6, which is directly adjacent to the chamber 16 shown in FIG. 5, experiences, by contrast, passage by heat-exchange medium flowing from the reactor space surrounding the contact tubes via the jacket aperture 6 through the lower inner ring line 13 and the open circular ring section 18. From the chamber 16, the heat-exchange medium is discharged through a firther open circular ring section 18 into the upper outer ring line 12 and from there to the pump(s).

FIG. 7 shows a preferred embodiment of the reactor according to the invention. In this embodiment, an additional bypass chamber 20 with a jacket aperture 21 to the reactor space and a regulating plate 22 are in each case arranged in at least some of the chambers 16 through which heat-exchange medium flows and is then discharged through the pump(s), in the region of the dividing wall of the chamber 16 to the upper outer ring line 12. The position of the regulating plate 22 can be adjusted in the direction of the longitudinal axis of the reactor via a suitable actuating drive and a drive spindle 23.

FIG. 8 shows a preferred embodiment of a reactor according to the invention having two heat-exchange medium circuits. The reactor is constructed analogously to a reactor having a single heat-exchange medium circuit corresponding to FIG. 1, right-hand side. In the second heat-exchange medium circuit, each of the features corresponding to the first heat-exchange medium circuit is designated by a corresponding reference numeral.

Analogously, it is possible to add further heat-exchange medium circuits to the reactor according to the invention. This enables the reactor to be matched optimally to the specific heat profile of each reaction to be carried out.

We claim:

1. A reactor (1) having a contact tube bindle (2) through whose space surrounding the contact tubes a heat-exchange medium circuit is passed, with ring lines (3, 4) at both ends of the reactor with jacket apertures (5, 6) for the supply and discharge of a heat-exchange medium by means of one or more pumps, wherein the heat-exchange medium or a sub-stream of the heat-exchange medium being passed through one or more external heat exchangers, the heat-exchange medium being fed to the lower ring line (4) and being fed back to the pump(s) via the upper ring line (3), and with baffle plates (7) which leave a passage cross section alternately in the reactor center and the reactor edge, wherein the upper (3) and lower (4) ring lines are each divided into an inner (11, 13) and outer (12, 14) ring line by means of a cylindrical partition wall (8, 9), and the heat-exchange medium is fed through the outer lower ring line (14), via a region outside the reactor to the inner upper ring line (11), via the latter's jacket apertures (5) to the space surrounding the contact tubes (2), via the jacket apertures (6) into the inner lower ring line (13) and subsequently via a region outside the reactor is discharged via the outer upper ring line (12).

2. A reactor (1) as claimed in claim 1, wherein the region between the lower (4) and upper (3) ring lines is closed by a cylinder envelope (15), forming a hollow cylinder, which is divided, by radial partition walls (17) perpendicular to the reactor base, into chambers (16) whose dividing walls to the ring lines (3, 4) leave alternately inner and outer circular ring sections, where, in plain view, an open circular ring section (18) is always arranged above a closed circular ring section (19), and vise versa.

3. A reactor as claimed in claim 2, wherein the number of chambers is from 12 to 96.

4. A reactor (1) as claimed in claim 1, wherein the diameter of the cylindrical partition walls (8, 9) is less than or equal to the arithmetic mean of the outer and inner diameters of the ring lines (3, 4).

5. A reactor (1) as claimed in claim 1, wherein a bypass chamber (20) with jacket aperture (21) to the reactor space and a regulating plate (22) is arranged in the region of the outer upper ring line (12) in each case in at least some of the chambers (16) through which heat-exchange medium flows and is discharged to the pump(s), the regulating plate (22) being adjustable in the direction of the longitudinal axis of the reactor via an actuating drive (24) and a drive spindle (23).

6. A reactor (1) as claimed in claim 1, wherein two or more heat-exchange medium circuits are passed through the space surrounding the contact tubes.

7. A reactor as claimed in claim 1 for use in carrying out oxidation reactions, in particular for the preparation of phthatic anhydride, maleic anhydride, glyoxal, (meth)acrolein or (meth)acrylic acid.

8. A reactor as claimed in claim 2, wherein the number of chambers is from 24 to 48.

* * * * *